(12) United States Patent
Elden et al.

(10) Patent No.: US 6,517,482 B1
(45) Date of Patent: Feb. 11, 2003

(54) METHOD AND APPARATUS FOR NON-INVASIVE DETERMINATION OF GLUCOSE IN BODY FLUIDS

(75) Inventors: Harry Richardson Elden, Miami, FL (US); Randall R. Wickett, Cincinnati, OH (US); Stig Ollmar, Champijonvagen (SE)

(73) Assignee: Dermal Therapy (Barbados) Inc. (BB)

( * ) Notice: Subject to any disclaimer, the term of this patent is extended or adjusted under 35 U.S.C. 154(b) by 0 days.

(21) Appl. No.: 09/601,705

(22) PCT Filed: Feb. 4, 1998

(86) PCT No.: PCT/US98/02037

§ 371 (c)(1),
(2), (4) Date: Nov. 1, 2000

(87) PCT Pub. No.: WO99/39627

PCT Pub. Date: Aug. 12, 1999

Related U.S. Application Data

(63) Continuation-in-part of application No. PCT/US97/13267, filed on Jul. 30, 1997, which is a continuation-in-part of application No. 08/688,650, filed on Jul. 30, 1996, now Pat. No. 5,890,489, which is a continuation-in-part of application No. 08/636,454, filed on Apr. 23, 1996, now abandoned.

(51) Int. Cl.[7] ............................................. A61B 5/00
(52) U.S. Cl. .................. 600/309; 600/347; 600/365
(58) Field of Search ............................ 600/316, 347, 600/365, 547, 309

(56) References Cited

U.S. PATENT DOCUMENTS

| | | | |
|---|---|---|---|
| 5,036,861 A | 8/1991 | Sembrowich et al. | |
| 5,115,133 A | 5/1992 | Knudson | |
| 5,146,091 A | 9/1992 | Knudson | |
| 5,179,951 A | 1/1993 | Knudson | |
| 5,222,496 A | 6/1993 | Clarke et al. | |
| 5,433,197 A | 7/1995 | Stark | |
| 5,508,203 A | * 4/1996 | Fuller et al. | 436/149 |
| 5,890,489 A | * 4/1999 | Elden | 128/898 |

FOREIGN PATENT DOCUMENTS

| | | |
|---|---|---|
| WO | WO 93/18402 | 9/1993 |
| WO | WO 95/04496 | 2/1995 |
| WO | WO 97/39341 | 10/1997 |

OTHER PUBLICATIONS

Zamazow et al. 4535 Asaio Transactions 36 (1990) Jul./Sep., No. 3, Toronto, CADevelopment and Evaluation of a Wearable Blood Glucose Monitor.

"Glucose entry into the human epidermis: II. The penetration of glucose into the human epidermis in vitro", K. M. Halprin and A. Ohkawara, *J. Invest. Derm.*, 49(6): 561, 1967.

"A microdialysis method allowing characterization of intercellular water space in human", P. Lonnroth, P.–A. Jansson and U. Smith, *The American Journal of Physiology*, 253 (Endocrinol. Metab., 16): E228–E231, 1987.

* cited by examiner

*Primary Examiner*—Eric F. Winakur
*Assistant Examiner*—Matthew Kremer
(74) *Attorney, Agent, or Firm*—Pennie & Edmonds LLP

(57) ABSTRACT

A method and apparatus is disclosed for non-invasively determining glucose levels in a fluid of a subject, typically the blood glucose level. The impedance of skin tissue is measured and the measurement is used with impedance measurements previously correlated with directly determined glucose levels to determine the glucose level from the newly measured impedance. It is thus possible, to routinely non-invasively determine fluid glucose levels.

125 Claims, 3 Drawing Sheets

METHOD AND APPARATUS FOR NON-INVASIVE DETERMINATION OF GLUCOSE IN BODY FLUIDS

This application is a 371 of PCT/US98/0237 filed Feb. 4, 1998 and a CIP of PCT/US97/13267 filed Jul. 30, 1997 which is a CIP Ser. No. 08/688,650 filed Jul. 30, 1996 U.S. Pat. No. 5,890,489, which is a CIP of Ser. No. 08/636,454 filed Apr. 23, 1996 abandoned.

FIELD OF THE INVENTION

The present invention relates to non-invasive methods and devices for determining the level of glucose in a body fluid of a subject.

BACKGROUND OF THE INVENTION

There are numerous reasons for determining the level of glucose present in body fluid of a subject. In the case of a person suffering from diabetes, it is often necessary to determine the glucose level in blood daily, or even more frequently. Non-invasive approaches to determination of blood glucose levels have been suggested in the patent literature. For example, U.S. Pat. No. 5,036,861 (issued to Sembrowich et al. on Aug. 6, 1991) describes a wrist-mountable device having an electrode which measures glucose present in sweat at the skin surface. U.S. Pat. No. 5,222,496 (issued to Clarke et al. on Jun. 29, 1993) describes an infrared glucose sensor mountable, for instance, on a wrist or finger. U.S. Pat. No. 5,433,197 (issued to Stark on Jul. 18, 1995) describes determination of blood glucose through illuminating a patient's eye with near-infrared radiation. U.S. Pat. Nos. 5,115,133, 5,146,091 and 5,197,951 (issued to Knudson on May 19, 1992, Sep. 8, 1992 and Jan. 19, 1993, respectively) describe measuring blood glucose within blood vessels of a tympanic membrane in a human ear through light absorption measurements. The specifications of all of these patents are incorporated herein by reference.

The most common current approaches to determining blood glucose levels still appear to involve obtaining a sample of the person's blood and then measuring the level of glucose in the sample. These approaches will not be reviewed here except to say that obtaining the blood sample necessarily involves an invasive technique. Generally, the person's skin is broken or lanced to cause an external flow of blood which is collected in some fashion for the glucose level determination. This can be both inconvenient and distressful for a person and it is an object of the present invention to avoid the step of obtaining a blood sample directly, at least on a routine or daily basis.

It is known that skin tissue, when immersed in an aqueous glucose solution, equilibrates linearly with the concentration of external glucose ("Glucose entry into the human epidermis. I. The Concentration of Glucose in the Human Epidermis", K. M. Halprin, A. Ohkawara and K. Adachi, *J. Invest. Dermatol.*, 49(6): 559, 1967; "Glucose entry into the human epidermis. II. The penetration of glucose into the human epidermis in vitro", K. M. Halprin and A. Ohkawara, *J. Invest. Derm.*, 49(6): 561, 1967). It has also been shown that skin glucose can vary in synchrony with blood level glucose during standardized tolerance testing in vivo ("The cutaneous glucose tolerance test I. A rate constant formula for glucose disappearance from the skin", R. M. Fusaro, J. A. Johnson and J. V. Pilsum, *J. Invest. Dermatol.*, 42: 359, 1964; "The cutaneous glucose tolerance test", R. M. Fusaro and J. A. Johnson, *J. Invest. Dermatol.*, 44: 230, 1965). It is also known for equilibration of glucose levels to occur between blood and interstitial fluids in contact with blood vessels ("A microdialysis method allowing characterization of intercellular water space in human", P. Lonnroth, P.-A. Jansson and U. Smith, *The American Journal of Physiology*, 253 (Endocrinol. Metab., 16): E228-E231, 1987; "Assessment of subcutaneous glucose concentration; validation of the wick technique as a reference for implanted electrochemical sensors in normal and diabetic dogs," U. Fischer, R. Ertle, P. Abel, K. Rebrin, E. Brunstein, H. Hahn von Dorsche and E. J. Freyse, *Diabetologia*, 30: 940, 1987). Implantation of dialysis needles equipped with glucose sensors has shown that orally ingested glucose load is reflected by parallel changes in skin tissue glucose.

Radio frequency spectroscopy using spectral analysis for in vitro or in vivo environments is disclosed in WO 9739341 (published Oct. 23, 1997) and WO 9504496 (published Feb. 16, 1995). Measurement of a target chemical such as blood glucose is described.

SUMMARY OF THE INVENTION

The present invention is a method and apparatus for non-invasively monitoring levels of glucose in a body fluid of a subject. Typically, blood glucose levels are determined in a human subject.

In a preferred embodiment, the invention is a method for non-invasively monitoring glucose in a body fluid of a subject in which the method includes steps of measuring impedance between two electrodes in conductive contact with a skin surface of the subject and determining the amount of glucose in the body fluid based upon the measured impedance. Typically, the body fluid in which it is desired to know the level of glucose is blood. In this way, the method can be used to assist in determining levels of insulin administration.

The step of determining the amount of glucose can include comparing the measured impedance with a predetermined relationship between impedance and blood glucose level, further details of which are described below in connection with preferred embodiments.

In a particular embodiment, the step of determining the blood glucose level of a subject includes ascertaining the sum of a fraction of the magnitude of the measured impedance and a fraction of the phase of the measured impedance. The amount of blood glucose, in one embodiment, is determined according to the equation: Predicted glucose=(0.31) Magnitude+(0.24)Phase where the impedance is measured at 20 kHz.

In certain embodiments, impedance is measured at a plurality of frequencies, and the method includes determining the ratio of one or more pairs of measurements and determining the amount of glucose in the body fluid includes comparing the determined ratio(s) with corresponding predetermined ratio(s), i.e., that have been previously correlated with directly measured glucose levels.

In certain embodiments, the method of the invention includes measuring impedance at two frequencies and determining the amount of glucose further includes determining a predetermined index, the index including a ratio of first and second numbers obtained from first and second of the impedance measurements. The first and second numbers can include a component of said first and second impedance measurements, respectively. The first number can be the real part of the complex electrical impedance at the first frequency and the second number can be the magnitude of the complex electrical impedance at the second frequency. The first number can be the imaginary part of the complex electrical impedance at the first frequency and the second number can be the magnitude of the complex electrical impedance at the second frequency. The first number can be the magnitude of the complex electrical impedance at the first frequency and the second number can be the magnitude of the complex electrical impedance at the second frequency. In another embodiment, determining the amount of glucose further includes determining a predetermined index in which the index includes a difference between first and second numbers obtained from first and second of said impedance measurements. The first number can be the phase angle of the complex electrical impedance at the first frequency and said second number can be the phase angle of the complex electrical impedance at the second frequency.

The skin site can be located on the volar forearm, down to the wrist, or it can be behind an ear of a human subject. Typically, the skin surface is treated with a saline solution prior to the measuring step. An electrically conductive gel can be applied to the skin to enhance the conductive contact of the electrodes with the skin surface during the measuring step.

The electrodes can be in operative connection with a computer chip programmed to determine the amount of glucose in the body fluid based upon the measured impedance. There can be an indicator operatively connected to the computer chip for indication of the determined amount of glucose to the subject. The indicator can. provide a visual display to the subject.

In certain embodiments, the computer chip is operatively connected to an insulin pump and the computer chip is programmed to adjust the amount of insulin flow via the pump to the subject in response to the determined amount of glucose.

Electrodes of a probe of the invention can be spaced between about 0.2 mm and about 2 cm from each other.

In another aspect, the invention is an apparatus for non-invasive monitoring of glucose in a body fluid of a subject. The apparatus includes means for measuring impedance of skin tissue in response to a voltage applied thereto and a microprocessor operatively connected to the means for measuring impedance, for determining the amount of glucose in the body fluid based upon the impedance measurement(s). The means for measuring impedance of skin tissue can include a pair of spaced apart electrodes for electrically conductive contact with a skin surface. The microprocessor can be programmed to compare the measured impedance with a predetermined correlation between impedance and blood glucose level. The apparatus can include means for measuring impedance at a plurality frequencies of the applied voltage and the programme can include means for determining the ratio of one or more pairs of the impedance measurements and means for comparing the determined ratio(s) with corresponding predetermined ratio(s) to determine the amount of glucose in the body fluid.

The apparatus preferably includes an indicator operatively connected to the microprocessor for indication of the determined amount of glucose. The indicator can provide a visual display for the subject to read the determined amount of glucose. It is possible that the indicator would indicate if the glucose level is outside of an acceptable range.

In a particular embodiment, the microprocessor is operatively connected to an insulin pump and the apparatus includes means to adjust the amount of insulin flow via the pump to the subject in response to the determined amount of glucose.

The apparatus can include a case having means for mounting the apparatus on the forearm of a human subject with the electrodes in electrically conductive contact with a skin surface of the subject.

In a particular embodiment, the apparatus includes means for calibrating the apparatus against a directly measured glucose level of a said subject. The apparatus can thus include means for inputting the value of the directly measured glucose level in conjunction with impedance measured about the same time, for use by the programme to determine the blood glucose level of that subject at a later time based solely on subsequent impedance measurements.

A microprocessor of the apparatus can be programmed to determine the glucose level of a subject based on the sum of a fraction of the magnitude of the measured impedance and a fraction of the phase of the measured impedance. In a particular embodiment, the apparatus is set to measure impedance at 20 kHz and the microprocessor is programmed to determine the glucose level of a subject based on the equation: Predicted glucose=(0.31)Magnitude+(0.24)Phase.

BRIEF DESCRIPTION OF THE DRAWINGS

Preferred embodiments of the invention will now be described, reference being had to the accompanying drawings, wherein:

FIG. 1(a) shows MIX versus measurement number, the timing of the measurements being given in Table 1. FIG. 1(b) shows PIX versus measurement number. FIG. 1(c) shows RIX versus measurement number. FIG. 1(d) shows IMIX versus measurement number. The determinations of MIX, PIX, RIX and IMIX are described in the text.

DETAILED DESCRIPTION OF PREFERRED EMBODIMENTS

A preferred method of the invention involves directly contacting a subject's skin with an electrode, taking one or more impedance measurements and determining the subject's blood glucose level based on the impedance measurement(s). Preferably, there is a computer programmed to make the determination based on the impedance measurement(s). In one aspect, the invention includes deriving a number of indices from one or more measurements of impedance between poles of the electrode. The value(s) of the one or more indices is an indicator of, i.e. correlates with, the subject's blood glucose level.

Thus, the invention is illustrated below by laboratory feasibility tests to establish that a correlation between one or more such index values based on impedance measurement(s) and a subject's blood glucose level exists. The tests were conducted using particular parameters, for example impedance measurements obtained at a certain frequency or certain frequencies, and particular indices were dervied there-from. It will be understood that other and/or additional frequencies may be found to be more optimal and that other indicies may well be found to be more optimal.

EXAMPLES

Each of two subjects was treated as indicated in Table 1. Impedance measurements were taken at the volar forearm using the "SCIM" apparatus described below. Impedance measurements were taken at thirty-one frequencies and four different indices were determined using two of the frequencies: 20 and 500 kHz. Directly measured blood glucose levels of each subject are indicated in Table 1.

TABLE 1

Treatment Regimen of Subjects

| Measurement No. - time (minutes) | Blood Glucose Measurement First Subject | Blood Glucose Measurement Second Subject |
|---|---|---|
| 0 | 154 | 141 |
| | Ingest 50 g glucose | |
| 1 | 10 | 146 | 164 |
| 2 | 20 | 174 | 194 |
| 3 | 30 | 246 | 232 |
| 4 | 40 | 228 | 257 |
| | Ingest 50 g glucose | |
| 5 | 50 | 268 | 304 |
| 6 | 60 | 255 | 348 |
| 7 | 70 | 320 | 346 |
| 8 | 80 | 320 | 355 |
| 9 | 90 | 399 | 361 |
| 10 | 100 | 343 | 383 |
| 11 | 110 | 334 | 381 |
| Rapid insulin administered | 4 units | 8 units |
| 12 | 125 | 358 | 379 |
| 13 | 140 | 377 | 346 |
| 14 | 155 | 353 | 333 |

Figure 1:
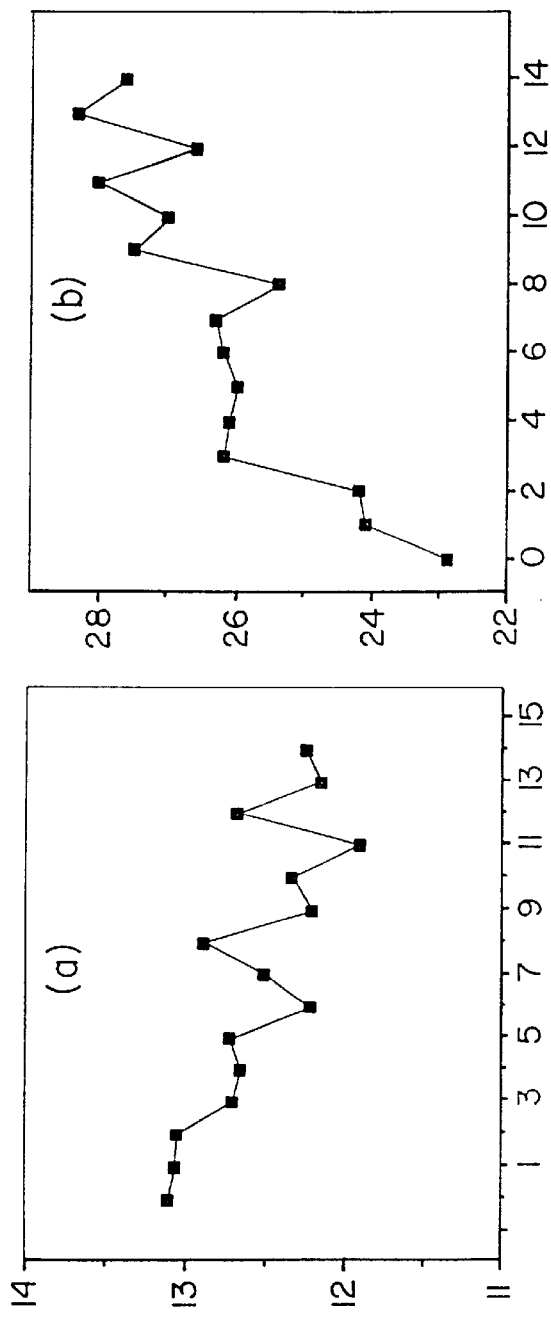
FIG. 1 shows plots of various indices as a function of time and glucose concentration based on impedance measurements taken on the skin (SCIM) of a first diabetic subject.
Figure 1:
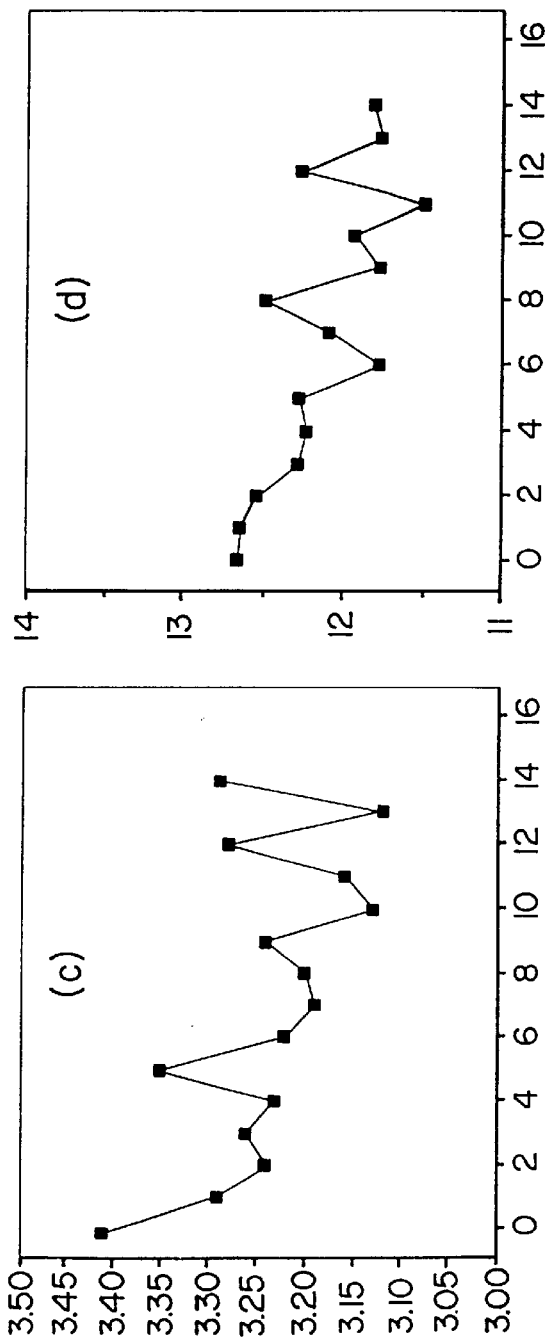
Figure 2:
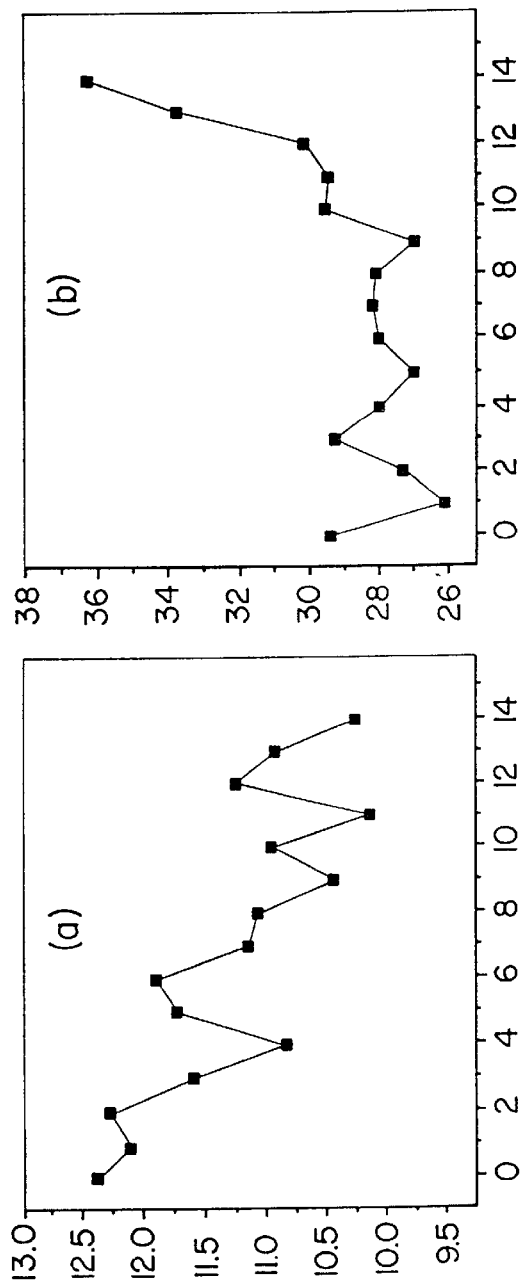
FIGS. 2(a), 2(b), 2(c) and 2(d) are similar to FIGS. 1(a) to 1(d), respectively, but are based on impedance measurement taken on the skin of a second diabetic subject.
Figure 2:
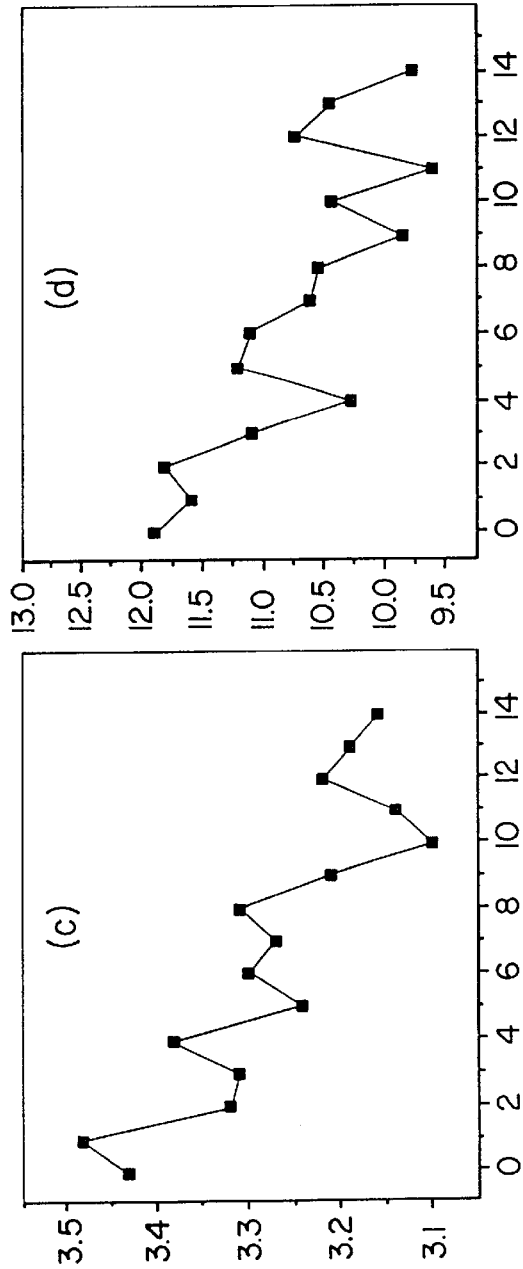

Four indices, MIX, PIX, RIX and IMIX were determined (see below) and plotted as a function of time. Results are shown in FIGS. 1 and 2, the data collected prior to the first glucose ingestion being assigned "0" on the x-axis of each plot.

Spearman rank order correlation coefficients were determined, and are presented Table 2 and 3 for the first and second subjects, respectively. A value of $P \leq 0.05$ is often considered to be a satisfactory correlation. As can be seen in Table 2, a satisfactory correlation was obtained for both the MIX and the IMIX indices for the first subject. As can be seen in Table 3, a satisfactory correlation was obtained for the MIX, PIX and IMIX indices for the second subject. The value of P for the RIX index was very close to being satisfactory. It must be borne in mind that these values were obtained from a small sample set and yet a clear indication of a satisfactory correlation for more than one index has been obtained in these experiments. Optimization of the parameters of frequency and the choice of index or indices might well lead to a significant improvement on the results given here.

TABLE 2

Statistical Analysis of Relationship between Measured Glucose Levels and Selected Indices for First Subject Spearman Rank Order Correlations

| Pair of Variables | Valid N | Spearman R | t(N − 2) | P |
|---|---|---|---|---|
| Glucose Level & MIX | 15 | −.722719 | −3.77028 | 0.002336 |
| Glucose Level & PIX | 15 | .865832 | 6.23942 | 0.000030 |
| Glucose Level & RIX | 15 | −.418980 | −1.66372 | 0.120073 |
| Glucose Level & IMIX | 15 | −.710833 | −3.64385 | 0.002972 |

TABLE 3

Statistical Analysis of Relationship between Measured Glucose Levels and Selected Indices for Second Subject Spearman Rank Order Correlations

| Pair of Variables | Valid N | Spearman R | t(N − 2) | P |
|---|---|---|---|---|
| Glucose Level & MIX | 15 | −.616622 | −2.82405 | 0.014353 |
| Glucose Level & PIX | 15 | .266547 | .99712 | 0.336903 |
| Glucose Level & RIX | 15 | −.477094 | −1.95731 | 0.072133 |
| Glucose Level & IMIX | 15 | −.607686 | −2.75888 | 0.016260 |

The impedance measurements on which the results shown in FIGS. 1 and 2 are based were obtained using a Surface Characterizing Impedance Monitor (SCIM) developed by Olimar (U.S. Pat. No. 5,353,802, issued Oct. 11, 1994; "Instrument evaluation of skin irritation", P. Y. Rizvi, B. M. Morrison, Jr., M. J. Grove and G. L. Grove, *Cosmetics & Toiletries.*, 111: 39, 1996; "Electrical impedance index in human skin: Measurements after occlusion, in 5 anatomical regions and in mild irritant contact dermatitis", L. Emtestam and S. Ollmar, *Cont. Derm.* 28: 337, 1975; "Electrical impedance for estimation of irritation in oral mucosa and skin", S. Ollmar, E. Eek, F. Sundstrom and L. Emtestam, *Medical Progress Through Technology*, 21: 29, 1995; "Electrical impedance compared with other non-invasive bioengineering techniques and visual scoring for detection of irritation in human skin", S. Ollmar, M. Nyren, I.'Nicander and L. Emtestam, *Brit. J. Dermatol.* 130: 29,1994; "Correlation of impedance response patterns to histological findings in irritant skin reactions induced by various surfactants", I. Nicander, S. Ollmar, A. Eek, B. Lundh Rozell and L. Emtestam, *Brit. J. Dermatol.* 134: 221, 1996) which measures bioelectrical impedance of the skin at multiple frequencies. The instrument is basically an AC-bridge fabricated from standard laboratory instruments: a function generator, a digital oscilloscope, impedance references, and a driver for the probe.

The indices plotted in FIGS. 1 and 2 were determined as follows:

MIX (magnitude index)=abs($Z_{20\ kHz}$)/abs($Z_{500\ kHz}$)

PIX (phase index)=arg($Z_{20\ kHz}$)−arg($Z_{500\ kHz}$)

RIX (real part index)=Re($Z_{20\ kHz}$)/abs($Z_{500\ kHz}$)

IMIX (imaginary part index)=Im($Z_{20\ kHz}$))/abs($Z_{500\ kHz}$)

where abs($Z_i$) is the magnitude (modulus) of the complex electrical impedance at the frequency i, arg($Z_i$) the argument (phase angle) in degrees, Re($Z_i$) the real part of the complex electrical impedance, and Im($Z_i$) the imaginary part of the complex electrical impedance. The magnitudes and phase angles are delivered by the instrument, and the real and imaginary parts are calculated according to the elementary complex number relationships: $Re(Z_i)=abs(Z_i)\cdot\cos[arg(Z_i)]$ and $Im(Z_i)=abs(Z_i)\cdot\sin[arg(Z_i)]$.

The RIX reflects changes mainly in conductivity; the IMIX reflects mainly reactance changes, which are of capacitive nature; the MIX reflects changes along the length of the vector describing the impedance in complex space, which will be emphasized if the real and imaginary parts change in the same direction and proportion; the PIX will be emphasized if the real and imaginary parts change in different directions and/or in different proportions.

Prior to contacting a subject's skin with the electrode, the skin is treated with a 0.9% saline solution by holding a soaked gauze against the measurement site for about a minute and then wiping the site with a dry cloth. The purpose of this step is to ensure adequate electrical coupling between the skin and the probe (electrode) in order to reduce variability that may introduced into the measurements by stratum corneum. A person skilled in the art would understand that variations are possible, and more optimal pre-treatment conditions may be obtainable.

Blood glucose levels were determined directly from a blood sample using a lancet prick and measuring the blood glucose concentration with an Elite Glucometer according to manufacturer's instructions (Elite Glucometer, Miles Canada, Diagnostics Division, Division of Bayer).

In a second set of experiments, 31 subjects were tested using the SCIM apparatus. A baseline measurement was taken and standardized food packet ingested. Two additional impedance measurements were taken one half hour and one hour after the initial measurement and blood glucose levels determined directly. Multiple regression analysis was carried out on data obtained at 20 kHz and relationship (1) established:

Predicted glucose=(0.31)Magnitude+(0.24)Phase; F-5.5, $p<0.005$

The multiple R for the prediction was 0.33.

The SCIM instrument was used to measure impedance measured at 31 different frequencies logarithmically distributed in the range of 1 kHz to 1 Mhz (10 frequencies per decade). Subsequent determinations were based, in the first set of experiments, on two of the frequencies: 20 and 500 kHz; and in the second set of experiments, 20 kHz only. It may be found in the future that there is a more optimal frequency or frequencies. It is quite possible, in a commercially acceptable instrument that impedance will be determined at at least two frequencies, rather than only one. For practical reasons of instrumentation, the upper frequency at which impedance is measured is likely to be about 500 kHz, but higher frequencies, even has high as 5 MHz or higher are possible and are considered to be within the scope of this invention. Relationships may be established using data obtained at one, two or more frequencies.

It may be found to be preferable to use an artificial neural network to perform a non-linear regression.

A preferred instrument, specifically for determining glucose levels of a subject, includes a 2-pole measurement configuration that measures impedance at multiple frequencies, preferably two well spaced apart frequencies. The instrument includes a computer which also calculates the index or indices that correlate with blood glucose levels and determines the glucose levels based on the corrlelation(s).

Figure 3:
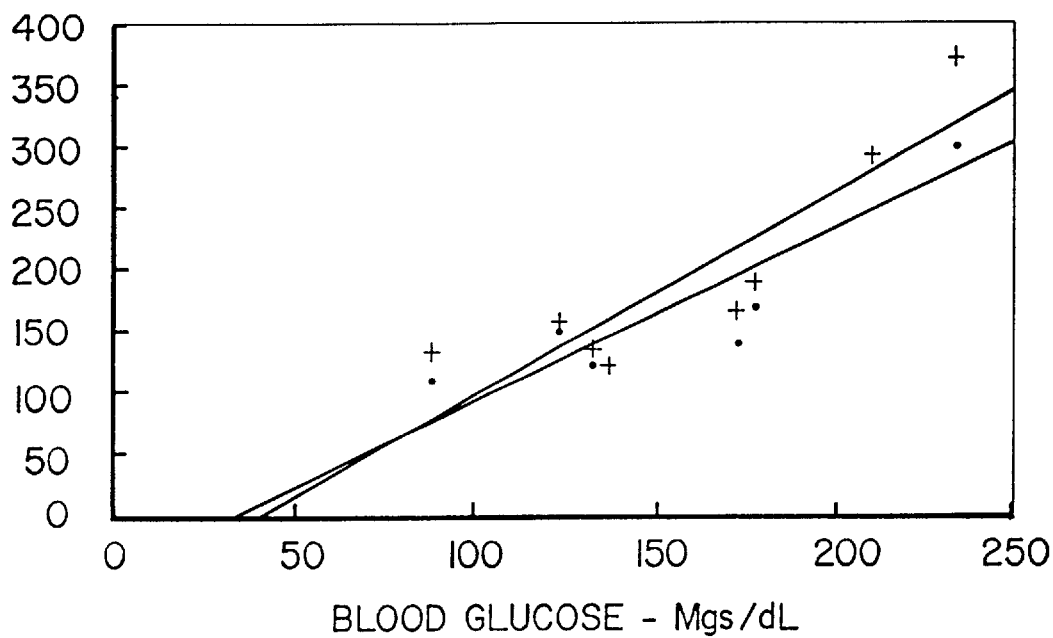
FIG. 3 is a plot showing the reading (average of ten readings) of a dermal phase meter as a function of directly determined blood glucose concentration. Measurements were taken on a site on the left forearm (.) and right forearm (+)
Figure 4:
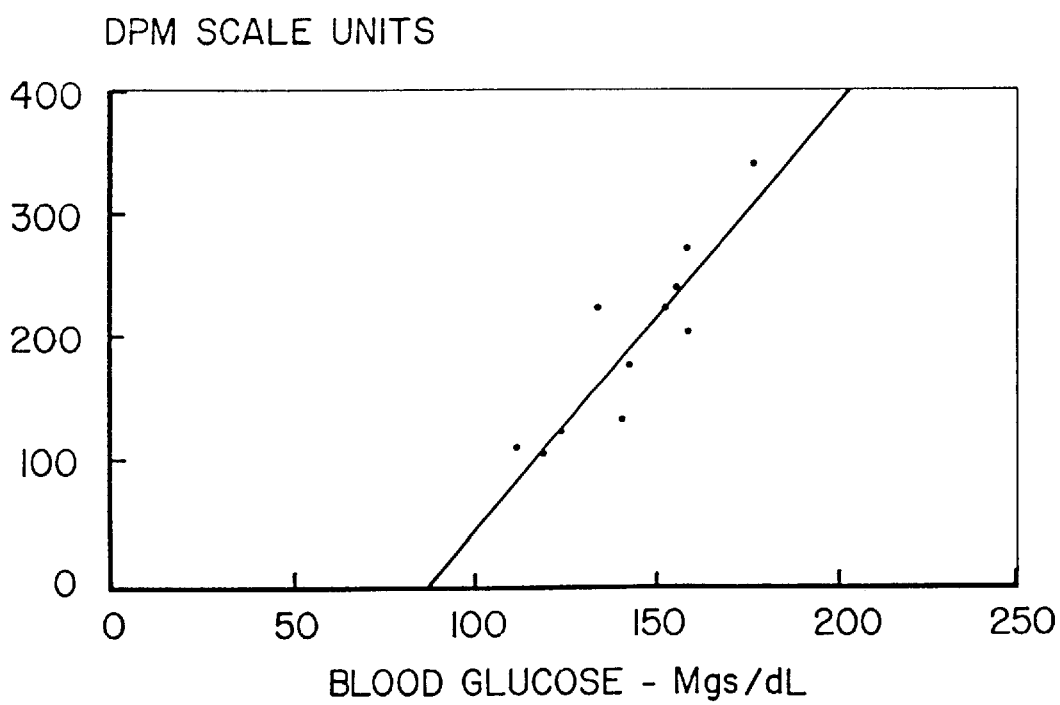
FIG. 4 is similar to FIG. 3, but readings were taken at a finger.

The invention is also illustrated by experiments that were carried out with a dermal phase meter (DPM) available from Nova™ Technology Corporation of Gloucester, Mass. Measurements were taken with the dermal phase meter at two skin sites, the forearm and the middle finger. The scale of the meter is from 90 to 999. It is thought that a higher reading indicates a higher degree of skin hydration. Blood glucose measurements were also measured directly (Mgs/dL) using an Elite Glucometer determined directly from a blood sample using a lancet prick and measuring the blood glucose concentration according to manufacturer's instructions (Elite Glucometer, Miles Canada, Diagnostics Division, Division of Bayer). Typical results are shown in FIGS. 3 and 4. Measurements were taken at various times to track changes in skin hydration from that present while fasting overnight, attending ingestion of a typical meal for breakfast or lunch and following a peak of blood glucose and decline to about 100 Mgs/dL.

In these experiments, a probe sensor was placed against the skin surface and held lightly until the instrument indicated completion of data acquisition. Time interval (latch time) for data acquisition was selected at zero seconds (instantaneous). Other suitable time periods can be anywhere 0 and 30 seconds, or between 0.5 and about 10 seconds, or between about 1 and 5 seconds or about 5 seconds. The results obtained using the dermal phase meter are plotted as function of blood glucose concentration in FIGS. 3 and 4, respectively. Each plotted point represents the average of 10 measurements using the dermal phase meter. Studies were performed in the morning on fasting subjects. After baseline measurements on fasting, food was ingested to raise blood glucose levels. Studies continued until blood glucose levels declined to baseline levels.

FIGS. 3 and 4 indicate that the Nova™ meter reading of the skin increases with increasing blood glucose concentration.

In one aspect of the invention, electrodes of a device are placed in conductive contact with a subject's skin in order to measure impedance (Z) at various frequencies (f) in a range from a few Hertz (hz) (say 10 hz) to about 5 Mhz. A more typical range would be between 1 kHz and 1 Mhz, and more likely between 5 kHz and 500 kHz. Electrodes of the device are electrically connected to a metering device which indicates the impedance at a selected frequency of applied voltage, as understood by a person skilled in the art. In a particular embodiment, the device is programmed to operate at the selected frequencies in rapid sequence. Alternative modes of operation are possible, for example, the voltage can be rapidly increased with time and Fourier transformation carried out to obtain a frequency spectrum. Ratios of impedance measured at various frequencies are determined and the blood glucose level of the subject is measured directly. This process is repeated at different times so as to make the determination at a number of different glucose levels. In this way, ratios of impedance determined at particular frequencies which are found to reproducibly reflect a person's blood glucose levels over a range of glucose levels are determined. The ratios of measured impedance at the selected frequencies can thus be correlated with directly measured glucose levels, that is, a plot in which $\log(Z_1/Z_2)$ vs log (f) is a linear correlation, or an approximately linear correlation, is determined. This relationship is then used to determine the blood glucose level of the person directly from ratios of similarly obtained impedance measurements, thus avoiding an invasive technique for obtaining the blood glucose level. Impedance includes both resistance and reactance.

It may be found for a proportion of the population that there is a universal set of impedance frequency ratios, thus avoiding the necessity of determining individual correlations.

The general approach described for the foregoing aspect of the invention can be used in connection with other indices based on impedance measurements, such as MIX, PIX, RIX and IMIX described above.

It is important, of course, to be able to reliably reproduce results as much as possible in order for this type of device to be useful. To this end an appropriate skin site is chosen. Generally speaking, an undamaged skin site and one that is not heavily scarred would be chosen. A skin site having a stratum corneum which is less likely to deleteriously interfere with the measurements is chosen. A likely possibility is the volar forearm, down to the wrist, or behind an ear. The skin surface can be treated just prior to measurement in order to render the stratum corneum more electrically transparent by application, for example, of a physiological saline dressing for about a minute. Excess liquid should be removed before application of the probe.

Given the importance of reliable glucose level determinations in setting insulin administrations, it is important that the invention be used only in circumstances in which it is known that the approach described herein reliably indicates glucose levels of a subject. It is possible that the invention would not be suitable for use with a given proportion of the population or 100% of the time with a given individual. For example, an individual may have a skin condition which deleteriously interferes with impedance measurements, making it difficult to assume that impedance measurements can reliably indicate a person's blood glucose level. For such a person, a different approach to glucose level determination would be more suitable.

An apparatus that utilizes a neural network to carry out analyses based on impedance could be trained for a specific subject, or possibly a group of subjects. An example of such a group of subjects might be subjects of the same sex, belonging to a particular age group and within particular height and weight ranges.

It may be advantageous to optimize the spacing of the electrodes of the probe. That is, it may found that the electrodes of a SCIM probe are too close to each other to provide maximally reproducible results. An object of a suitable probe is to have electrodes spaced from each other to obtain optimal penetration of current into tissue containing glucose in its interstitial spaces. It is expected that electrodes spaced somewhere between about 0.2 mm and about 2 cm are suitable.

Additionally, the use of a gel can improve skin-probe contact to more reliably produce useful measurements, as would be known to a person skilled in the art, e.g., a gel comprising mostly water in combination with a thickener such as Cellusize, glycerin or propylene glycol as a moisturizer, and a suitable preservative.

An apparatus for non-invasive monitoring of glucose in a body fluid of a subject includes means for measuring impedance of skin tissue in response to a voltage applied thereto, i.e. a probe. There is a computer processor operatively connected to the means for measuring impedance for determining the blood glucose level based upon one or more impedance measurements. The microprocessor is programmed to calculate the blood glucose level of a subject based upon impedance measurements taken at one or more frequencies. In a particular embodiment, a calcuation based upon impedance at a single frequency, along the lines of that shown in relationship (1), is carried out by the processor. In another embodiment, the calculation includes determining MIX and/or IMIX. The calculation might include determining PIX. The calculation might include determining RIX. It might be necessary to calibrate an individual apparatus for use with a particular subject. In such case, the apparatus includes means for calibrating the apparatus against a directly measured glucose level of that subject. The apparatus could thus include means for inputting the value of the directly measured glucose level in conjunction with impedance measured about the same time, for use by the programme to determine the blood glucose level of that subject at a later time based solely on subsequent impedance measurements.

In one embodiment, a meter is worn in which a probe is continuously in contact with the skin and moisture buildup between occlusive electrodes and the skin is sufficient to obtain useful measurements. The device can be mountable on a person's forearm, much like a wristwatch. Such an embodiment might not prove to be useful for all subjects.

As previously stated, it might be found to be necessary for a meter to be calibrated individually, that is, it might be necessary to determine the relationship between ascertained impedance ratios or index or indices of interest, and blood glucose levels of an individual and base the operation of the particular meter for that individual on the relationship. To this end, a preferred monitoring device of the invention includes means for calibrating the relationship between a directly measured blood glucose level and an index or indices of interest.

Because blood glucose level determinations of the present invention are non-invasive and relatively painless it is possible to make such determinations with a greater frequency than with a conventional pin-prick method. In a particularly advantageous embodiment, blood glucose levels are monitored quite frequently, say every fifteen or five, or even one minute or less, and an insulin pump is interfaced with the meter to provide continual control of blood glucose in response to variations of blood glucose levels ascertained by means of the meter.

The disclosures of all references, and particularly the specifications of all patent documents, referred to herein, are incorporated herein by reference.

The invention now having been described, including the best mode currently known to the inventors, the claims which define the scope of the protection sought for the invention follow.

What is claimed is:

1. A method for non-invasively monitoring glucose in a body fluid of a subject, the method comprising:
    measuring impedance between two electrodes in conductive contact with a skin surface of the subject at a plurality of frequencies wherein all said frequencies are in a range from about 10 Hz to about 5 MHZ; and
    determining the amount of glucose in the body fluid based upon the measured impedance.

2. The method of claim 1, wherein the skin surface is treated with a saline solution prior to the measuring step, and the body fluid is blood.

3. The method of claim 1, wherein the subject is human and the body fluid is blood.

4. The method of claim 3, wherein determining the amount of glucose includes comparing the measured impedance with a predetermined relationship between impedance and blood glucose level.

5. The method of claim 4, including the step of determining the ratio of one or more pairs of measurements, and wherein determining the amount of glucose in the body fluid includes comparing the determined ratio(s) with corresponding predetermined ratio(s).

6. The method of claim 5, wherein the skin surface is located on the a volar forearm.

7. The method of claim 6, wherein an electrically conductive gel is applied to the skin to enhance conductive contact of the electrodes with the skin surface during the measuring step.

8. The method of claim 7, wherein the electrodes are in operative connection with a computer chip programmed to determined the amount of glucose in the body fluid based upon the measured impedance.

9. The method of claim 8, wherein an indicator is operatively connected to the computer chip for indication of the determined amount of glucose to the subject, and the indicator provides a visual display to the subject.

10. The method of claim 9, wherein the computer chip is operatively connected to an insulin pump and the computer chip is further programmed to adjust the amount of insulin flow via the pump to the subject in response to the determined amount of glucose.

11. The method of claim 3, wherein the electrodes are spaced between about 0.2 mm and about 2 cm from each other.

12. The method of claim 1 wherein determining the amount of glucose further includes determining a predetermined index, the index comprising a difference between first and second numbers obtained from first and second of said impedance measurements.

13. The method of claim 12, wherein said first number is the phase angle of the complex electrical impedance at the first frequency and said second number is the phase angle of the complex electrical impedance at the second frequency.

14. The method of claim 1, wherein determining the amount of glucose includes ascertaining the sum of a fraction of the magnitude of the measured impedance and a fraction of the phase of the measured impedance.

15. The method of claim 1, wherein a saline solution is applied just prior to measuring impedance so as to render the stratum corneum more electrically transparent.

16. The method of claim 15, wherein said saline solution is a physiological saline solution.

17. The method of claim 16, wherein said saline solution is about 0.09% saline.

18. The method of claim 17, wherein said saline solution is applied against a measurement site for about a minute.

19. The method of claim 1, wherein determining the amount of glucose further includes determining a predetermined index, the index comprising a ratio of first and second numbers obtained from first and second of said impedance measurements.

20. The method of claim 19 wherein each of said first and second numbers includes a component of said first and second impedance measurements, respectively.

21. The method of claim 20 wherein said first number is the real part of the complex electrical impedance at the first frequency and the second number is the magnitude of the complex electrical impedance at the second frequency.

22. The method of claim 20 wherein said first number is the imaginary part of the complex electrical impedance at the first frequency and the second number is magnitude of the complex electrical impedance at the second frequency.

23. The method of claim 20 wherein said first number is the magnitude of the complex electrical impedance at the first frequency and said second number is the magnitude of the complex electrical impedance at the second frequency.

24. A method for non-invasively monitoring glucose in a body fluid of a subject, the method comprising:
    measuring impedance between two electrodes in conductive contact with a skin surface of the subject at a plurality of frequencies wherein at least one of the frequencies is below about 100 kHz; and
    determining the amount of glucose in the body fluid based upon the measured impedance.

25. The method of claim 24, wherein the skin surface is treated with a saline solution prior to the measuring step, and the body fluid is blood.

26. The method of claim 24, wherein the subject is human and the body fluid is blood.

27. The method of claim 26, wherein determining the amount of glucose includes comparing the measured impedance with a predetermined relationship between impedance and blood glucose level.

28. The method of claim 27, including the step of determining the ratio of one or more pairs of measurements, and wherein determining the amount of glucose in the body fluid includes comparing the determined ratio(s) with corresponding predetermined ratio(s).

29. The method of claim 28, wherein the skin surface is located on a volar forearm.

30. The method of claim 29, wherein an electrically conductive gel is applied to the skin to enhance conductive contact of the electrodes with the skin surface during the measuring step.

31. The method of claim 30, wherein the electrodes are in operative connection with a computer chip programmed to determine the amount of glucose in the body fluid based upon the measured impedance.

32. The method of claim 31, wherein an indicator is operatively connected to the computer chip for indication of the determined amount of glucose to the subject, and the indicator provides a visual display to the subject.

33. The method of claim 32, wherein the computer chip is operatively connected to an insulin pump and the computer chip is further programmed to adjust the amount of insulin flow via the pump to the subject in response to the determined amount of glucose.

34. The method of claim 26, wherein the electrodes are spaced between about 0.2 mm and about 2 cm from each other.

35. The method of claim 24 wherein determining the amount of glucose further includes determining a predetermined index, the index comprising a ration of first and second numbers obtained from first and second of said impedance measurements.

36. The method of claim 35 wherein each of said first and second numbers includes a component of said first and second impedance measurements, respectively.

37. The method of claim 36 wherein said first number is the real part of the complex electrical impedance at the first frequency and the second number is the magnitude of the complex electrical impedance at the second frequency.

38. The method of claim 36 wherein said first number is the imaginary part of the complex electrical impedance at the first frequency and the second number is magnitude of the complex electrical impedance at the second frequency.

39. The method of claim 36 wherein said first number is the magnitude of the complex electrical impedance at the first frequency and said second number is the magnitude of the complex electrical impedance at the second frequency.

40. The method of claim 24 wherein determining the amount of glucose further includes determining a predetermined index, the index comprising a difference between first and second numbers obtained from first and second of said impedance measurements.

41. The method of claim 40, wherein said first number is the phase angle of the complex electrical impedance at the first frequency and said second number is the phase angle of the complex electrical impedance at the second frequency.

42. The method of claim 24, wherein determining the amount of glucose includes ascertaining the sum of a fraction of the magnitude of the measured impedance and a fraction of the phase of the measured impedance.

43. The method of claim 24, wherein a saline solution is applied just prior to measuring impedance so as to render the stratum corneum more electrically transparent.

44. The method of claim 43, wherein said saline solution is a physiological saline solution.

45. The method of claim 44, wherein said saline solution is about 0.9% saline.

46. The method of claim 45, wherein said saline solution is applied against a measurement site for about a minute.

47. A method for non-invasively monitoring glucose in a body fluid of a subject, the method comprising:
    measuring impedance between two electrodes in conductive contact with a skin surface of the subject at a plurality of frequencies wherein at least one of the frequencies is about 20 kHz; and
    determining the amount of glucose in the body fluid based upon the measured impedance.

48. The method of claim 47, wherein the skin surface is treated with a saline solution prior to the measuring step, and the body fluid is blood.

49. The method of claim 47, wherein the subject is human and the body fluid is blood.

50. The method of claim 49, wherein determining the amount of glucose includes comparing the measured impedance with a predetermined relationship between impedance and blood glucose level.

51. The method of claim 50, including the step of determining the ratio of one or more pairs of measurements, and wherein determining the amount of glucose in the body fluid includes comparing the determined ratio(s) with corresponding predetermined ratio(s).

52. The method of claim 51, wherein the skin surface is located on a volar forearm.

53. The method of claim 52, wherein an electrically conductive gel is applied to the skin to enhance conductive contact of the electrodes with the skin surface during the measuring step.

54. The method of claim 53, wherein the electrodes are in operative connection with a computer chip programmed to determine the amount of glucose in the body fluid based upon the measured impedance.

55. The method of claim 54, wherein an indicator is operatively connected to the computer chip for indication of the determined amount of glucose to the subject, and the indicator provides a visual display to the subject.

56. The method of claim 55, wherein the computer chip is operatively connected to an insulin pump and the computer chip is further programmed to adjust the amount of insulin flow via the pump to the subject in response to the determined amount of glucose.

57. The method of claim 49, wherein the electrodes are spaced between about 0.2 mm and about 2 cm from each other.

58. The method of claim 47 wherein determining the amount of glucose further includes determining a predetermined index, the index comprising a ratio of first and second numbers obtained from first and second of said impedance measurements.

59. The method of claim 58 wherein each of said first and second numbers includes a component of said first and second impedance measurements, respectively.

60. The method of claim 59 wherein said first number is the real part of the complex electrical impedance at the fist frequency and the second number is the magnitude of the complex electrical impedance at the second frequency.

61. The method of claim 59 wherein said first number is the imaginary part of the complex electrical impedance at the first frequency and the second number is magnitude of the complex electrical impedance at the second frequency.

62. The method of claim 59 wherein said first number is the magnitude of the complex electrical impedance at the first frequency and said second number is the magnitude of the complex electrical impedance at the second frequency.

63. The method of claim 47 wherein determining the amount of glucose further includes determining a predetermined index, the index comprising a difference between first and second numbers obtained from first and second of said impedance measurements.

64. The method of claim 63, wherein said first number is the phase angle of the complex electrical impedance at the first frequency and said second number is the phase angle of the complex electrical impedance at the second frequency.

65. The method of claim 47, wherein determining the amount of glucose includes ascertaining the sum of a fraction of the magnitude of the measured impedance and a fraction of the phase of the measured impedance.

66. The method of claim 47, wherein a saline solution is applied just prior to measuring impedance so as to render the stratum corneum more electrically transparent.

67. The method of claim 66, wherein said saline solution is a physiological saline solution.

68. The method of claim 67, wherein said saline solution is about 0.9% saline.

69. The method of claim 68, wherein said saline solution is applied against a measurement site for about a minute.

70. A method for non-invasively monitoring glucose in a body fluid of a subject, the method comprising:
    treating a surface of the skin of the subject with a saline solution and wiping the treated surface to reduce variability that may be introduced into impedance measurements by the stratum corneum;
    measuring impedance between two electrodes in conductive contact with the skin surface; and
    determining the amount of glucose in the body fluid based upon the measured impedance.

71. The method of claim 70 wherein said saline solution is applied just prior to measuring impedance so as to render the stratum corneum more electrically transparent.

72. The method of claim 70 wherein the body fluid is blood and the subject is human.

73. The method of 72 wherein determining the amount of glucose includes comparing the measured impedance with a predetermined relationship between impedance and blood glucose level.

74. The method of claim 70, including measuring impedance at a plurality of frequencies, determining the ratio of one or more pairs of measurements and wherein determining the amount of glucose in the body fluid includes comparing the determined ratio(s) with corresponding predetermined ratio(s).

75. The method of claim 74 wherein the skin surface is located on a volar forearm.

76. The method of claim 70 wherein an electrically conductive gel is applied to the skin to enhance conductive contact of the electrodes with the skin surface during the measuring step.

77. The method of claim 76, wherein the electrodes are in operative connection with a computer chip programmed to determine the amount of glucose in the body fluid based upon the measured impedance.

78. The method of claim 77, wherein an indicator is operatively connected to the computer chip for indication of the determined amount of glucose to the subject, and the indicator provides a visual display to the subject.

79. The method of claim 78, wherein the computer chip is operatively connected to an insulin pump and the computer chip is further programmed to adjust the amount of insulin flow via the pump to the subject in response to the determined amount of glucose.

80. The method of claim 70, wherein the electrode are spaced between about 0.2 mm and about 2 cm from each other.

81. The method of claim 70 wherein determining the amount of glucose includes measuring impedance at two frequencies.

82. The method of claim 81 wherein determining the amount of glucose further includes determining a predetermined index, the index comprising a ratio of first and second numbers obtained from first and second of said impedance measurements.

83. The method of claim 82 wherein each of said first and second numbers includes a component of said first and second impedance measurements, respectively.

84. The method of claim 83 wherein said first number is the real part of the complex electrical impedance at the first frequency and the second number is the magnitude of the complex electrical impedance at the second frequency.

85. The method of claim 83 wherein said first number is the imaginary part of the complex electrical impedance at the first frequency and the second number is magnitude of the complex electrical impedance at the second frequency.

86. The method of claim 83 wherein said first number is the magnitude of the complex electrical impedance at the first frequency and said second number is the magnitude of the complex electrical impedance at the second frequency.

87. The method of claim 81 wherein determining the amount of glucose further includes determining a predetermined index, the index comprising a difference between first and second numbers obtained from first and second of said impedance measurements.

88. The method of claim 87 wherein said first number is the phase angle of the complex electrical impedance at the first frequency and said second number is the phase angle of the complex electrical impedance at the second frequency.

89. The method claim 70 wherein determining the amount of glucose includes ascertaining the sum of a fraction of the magnitude of the measured impedance and a fraction of the phase of the measured impedance.

90. The method of claim 70, wherein said saline solution is a physiological saline solution.

91. The method of claim 70, wherein said saline solution is about 0.9% saline.

92. The method of claim 70, wherein said saline solution is applied against a measurement site for about a minute.

93. An apparatus for non-invasive monitoring of glucose in a body fluid of a subject, the apparatus comprising:
means for measuring impedance of skin tissue, at a plurality of frequencies wherein all said frequencies are in a range from about 10 Hz to about 5 MHZ, in response to a voltage applied thereto; and
a microprocessor operatively connected to the means for measuring impedance, for determining the amount of glucose in the body fluid based upon the impedance measurement.

94. The apparatus of claim 93, wherein said means for measuring impedance of skin tissue includes a pair of spaced apart electrodes for electrically conductive contact with a skin surface.

95. The apparatus of claim 94, wherein said microprocessor is programmed to compare the measured impedance with a predetermined correlation between impedance and blood glucose level.

96. The apparatus of claim 95, including means for measuring impedance at a plurality of frequencies of said applied voltage, wherein said microprocessor is further programmed to determine the ratio of one or more pairs of the impedance measurements and means for comparing the determined ratio(s) with corresponding predetermined ratio(s) to determine the amount of glucose in the body fluid.

97. The apparatus of claim 94, wherein the electrodes are spaced between about 0.2 mm and about 2 cm from each other.

98. The apparatus of claim 94, including a case having means for mounting the apparatus on a forearm of a human subject with the electrodes in said electrically conductive contact with a skin surface of the subject.

99. The apparatus of claim 93, further comprising an indicator operatively connected to the microprocessor for indication of the determined amount of glucose.

100. The apparatus of claim 99, wherein the indicator provides a visual display.

101. The apparatus of claim 99, wherein the microprocessor is operatively connected to an insulin pump and includes means to adjust the amount of insulin flow via the pump to the subject in response to the determined amount of glucose.

102. The apparatus of claim 93, further comprising:
means for calibrating the apparatus against a directly measured glucose level of a said subject.

103. The apparatus of claim 93, wherein the microprocessor is programmed to determine the glucose level of a subject based on the sum of a fraction of the magnitude of the measured impedance and a fraction of the phase of the measured impedance.

104. An apparatus for non-invasive monitoring of glucose in a body fluid of a subject, the apparatus comprising:
means for measuring impedance of skin tissue, at a plurality of frequencies wherein at least one of the frequencies is below about 100 kHz, in response to a voltage supplied thereto; and
a microprocessor operatively connected to the means for measuring impedance, for determining the amount of glucose in the body fluid based upon the impedance measurement.

105. The apparatus of claim 104, wherein said means for measuring impedance of skin tissue includes a pair of spaced apart electrodes for electrically conductive contact with a skin surface.

106. The apparatus of claim 105, wherein said microprocessor is programmed to compare the measured impedance with a predetermined correlation between impedance and blood glucose level.

107. The apparatus of claim 106, including means for measuring impedance at a plurality of frequencies of said applied voltage, wherein said microprocessor is further programmed to determine the ratio of one or more pairs of the impedance measurements and means for comparing the determined ratio(s) with corresponding predetermined ratio(s) to determine the amount of glucose in the body fluid.

108. The apparatus of claim 105, wherein the electrodes are spaced between about 0.2 mm and about 2 cm from each other.

109. The apparatus of claim 105, including a case having means for mounting the apparatus on a forearm of a human subject with the electrodes in said electrically conductive contact with a skin surface of the subject.

110. The apparatus of claim 104, further comprising an indicator operatively connected to the microprocessor for indication of the determined amount of glucose.

111. The apparatus of claim 110, wherein the indicator provides a visual display.

112. The apparatus of claim 110, wherein the microprocessor is operatively connected to an insulin pump and includes means to adjust the amount of insulin flow via the pump to the subject in response to the determined amount of glucose.

113. The apparatus of claim 104, further comprising:
   means for calibrating the apparatus against a directly measured glucose level of a said subject.

114. The apparatus of claim 104, wherein the microprocessor is programmed to determine the glucose level of a subject based on the sum of a fraction of the magnitude of the measured impedance and a fraction of the phase of the measured impedance.

115. An apparatus for non-invasive monitoring of glucose in a body fluid of a subject, the apparatus comprising:
   means for measuring impedance of skin tissue, at a plurality of frequencies wherein at least one of the frequencies is about 20 kHz, in response to a voltage applied thereto; and
   a microprocessor operatively connected to the means for measuring impedance, for determining the amount of glucose in the body fluid based upon the impedance measurement.

116. The apparatus of claim 115, wherein said means for measuring impedance of skin tissue includes a pair of spaced apart electrodes for electrically conductive contact with a skin surface.

117. The apparatus of claim 116, wherein said microprocessor is programmed to compare the measured impedance with a predetermined correlation between impedance and blood glucose level.

118. The apparatus of claim 117, including means for measuring impedance at a plurality of frequencies of said applied voltage, wherein said microprocessor is further programmed to determine the ratio of one or more pairs of the impedance measurements and means for comparing the determined ratio(s) with corresponding predetermined ratio(s) to determine the amount of glucose in the body fluid.

119. The apparatus of claim 116, including a case having means for mounting the apparatus on a forearm of a human subject with the electrodes in said electrically conductive contact with a skin surface of the subject.

120. The apparatus of claim 115, further comprising an indicator operatively connected to the microprocessor for indication of the determined amount of glucose.

121. The apparatus of claim 120, wherein the indicator provides a visual display.

122. The apparatus of claim 120, wherein the microprocessor is operatively connected to an insulin pump and includes means to adjust the amount of insulin flow via the pump to the subject in response to the determined amount of glucose.

123. The apparatus of claim 116, wherein the electrodes are spaced between about 0.2 mm and about 2 cm from each other.

124. The apparatus of claim 115, further comprising:
   means for calibrating the apparatus against a directly measured glucose level of a said subject.

125. The apparatus of claim 115, wherein the microprocessor is programmed to determine the glucose level of a subject based on the sum of a fraction of the magnitude of the measured impedance and a fraction of the phase of the measured impedance.

* * * * *

UNITED STATES PATENT AND TRADEMARK OFFICE
CERTIFICATE OF CORRECTION

PATENT NO. : 6,517,482 B1  
DATED : February 11, 2003  
INVENTOR(S) : Harry Richardson Elden, Randall R. Wickett and Stig Ollmar Page 1 of 1

It is certified that error appears in the above-identified patent and that said Letters Patent is hereby corrected as shown below:

Column 1,  
Line 5, replace "PCT/US98/0237" with -- PCT/US98/02037 --.

Column 10,  
Line 65, delete "the".

Column 11,  
Line 5, replace "determined" with -- determine --.  
Line 37, replace "0.09%" with -- 0.9% --.

Column 12,  
Line 39, replace "ration" with -- ratio --.

Column 15,  
Line 8, replace "electrode" with -- electrodes --.  
Line 42, after "The method", insert -- of --.

Signed and Sealed this

Twenty-fourth Day of June, 2003

JAMES E. ROGAN  
*Director of the United States Patent and Trademark Office*